United States Patent
Percival et al.

(12) 
(10) Patent No.: US 6,749,302 B2
(45) Date of Patent: Jun. 15, 2004

(54) AFOCAL POSITION DETECTION SYSTEM AND OPHTHALMIC INSTRUMENT EMPLOYING SAID SYSTEM

(75) Inventors: Christopher J. Percival, Williamsville, NY (US); Douglas H. Hoover, Corfu, NY (US)

(73) Assignee: Reichert, Inc., Depew, NY (US)

( * ) Notice: Subject to any disclaimer, the term of this patent is extended or adjusted under 35 U.S.C. 154(b) by 400 days.

(21) Appl. No.: 09/992,497

(22) Filed: Nov. 6, 2001

(65) Prior Publication Data

US 2003/0086058 A1 May 8, 2003

(51) Int. Cl.⁷ .................................................. A61B 3/14
(52) U.S. Cl. ........................ 351/208; 351/209; 351/210; 351/246; 600/399
(58) Field of Search ......................... 351/208, 205, 351/206, 211, 218, 209, 210, 246, 221; 250/206.2; D24/172; 600/398, 399, 561, 401, 405, 587

(56) References Cited

U.S. PATENT DOCUMENTS

| | | | |
|---|---|---|---|
| 3,585,849 A | | 6/1971 | Grolman |
| 3,756,073 A | | 9/1973 | Lavallee et al. |
| 4,817,620 A | * | 4/1989 | Katsuragi et al. ........... 600/401 |
| 4,881,807 A | | 11/1989 | Luce et al. |
| 5,446,274 A | * | 8/1995 | Luce et al. ............... 250/206.2 |
| 5,565,939 A | * | 10/1996 | Fujieda ...................... 351/205 |
| 5,629,747 A | * | 5/1997 | Miyake ...................... 351/218 |
| 5,865,742 A | * | 2/1999 | Massie ...................... 600/405 |
| 6,159,148 A | | 12/2000 | Luce |
| 6,361,495 B1 | * | 3/2002 | Grolman ..................... 600/401 |
| D468,430 S | * | 1/2003 | Hoelbl ...................... D24/172 |
| 6,623,429 B2 | * | 9/2003 | Percival et al. ............. 600/399 |
| 6,669,340 B2 | * | 12/2003 | Percival et al. ............. 351/208 |
| 6,685,318 B2 | * | 2/2004 | Kohayakawa ............... 351/208 |

FOREIGN PATENT DOCUMENTS

EP  1121895  8/2001

* cited by examiner

Primary Examiner—Henry Bennett
Assistant Examiner—Fadi H. Dahbour
(74) Attorney, Agent, or Firm—Hodgson Russ LLP

(57) ABSTRACT

A fast position detection system and related method for an ophthalmic instrument utilize stored geometrical relationships determined by multiple regression during instrument calibration to compute X-Y-Z alignment status of the instrument relative to a patient's eye based on local x-y position information from a pair of lateral detectors receiving corneally reflected light from a corresponding pair of lateral light sources. In a preferred embodiment, the lateral detectors are quad-cell detectors. A heads-up display image is preferably provided along an optical axis of the instrument for supplying instructive cues to an operator for moving the instrument to achieve alignment, whereby the operator sees both a macro-image of the patient's eye and the display image. The speed of the position detection system makes it particularly suitable for use in hand-held ophthalmic instruments.

24 Claims, 6 Drawing Sheets

AFOCAL POSITION DETECTION SYSTEM AND OPHTHALMIC INSTRUMENT EMPLOYING SAID SYSTEM

BACKGROUND OF THE INVENTION

I. Field of the Invention

The present invention relates generally to opto-electronic position detection systems for providing information regarding the three-dimensional alignment status of an ophthalmic instrument relative to an eye of a patient, and more particularly to an afocal position detection system capable of providing updated position information at a very high rate of repetition.

II. Description of the Related Art

Opto-electronic position detection and alignment systems for use in locating an ophthalmic instrument relative to an eye to be tested are well known, as evidenced by U.S. Pat. No. 4,881,807 to Luce et al. Where the ophthalmic instrument is a non-contact tonometer having a discharge tube for directing a fluid pulse at the eye, X-Y alignment is typically achieved by aligning an axis of the discharge tube to intersect with the corneal vertex, and Z alignment is achieved by positioning a fluid exit end of the discharge tube at a predetermined distance from the corneal vertex. In systems of the prior art, triangulation is used to gauge the three-dimensional location of the eye relative to the instrument. By way of example, the aforementioned U.S. Pat. No. 4,881,807 discloses a system wherein two light sources arranged on opposite sides of the eye illuminate the eye with divergent rays, and a pair of CCD area detectors each comprising a two-dimensional array of light-sensitive pixels are arranged behind associated pinhole apertures to receive a small bundle of reflected rays originating from a corresponding one of the light sources. A local x-y location where the light strikes the CCD array is determined by identifying the pixel registering the peak response signal. The local x-y locations where light strikes each CCD array and specifications describing the predetermined geometric arrangement of the system components are provided as inputs to a microprocessor, which then calculates the amount of movement in the global X, Y, and Z directions necessary to achieve alignment.

While the system described above has proved suitable for use in large table mounted instruments where the patient's head is stabilized by a forehead rest to minimize inadvertent relative movement between the instrument and the eye, the fact that a large number of CCD pixels must be scanned to make a single position determination introduces a limitation as to the repetition rate of the system that makes the system too slow for use in smaller hand-held ophthalmic instruments, where inadvertent relative motion between the instrument and the eye is constantly taking place as the operator aligns the instrument by hand. Moreover, the system of U.S. Pat. No. 4,881,807 and other prior art systems like it are expensive to manufacture because of the types and number of optical and opto-electronic elements necessary, and the dimensional criticality in positioning these elements with respect to one another.

BRIEF SUMMARY OF THE INVENTION

Therefore, it is an object of the present invention to provide a position detection system and method for an ophthalmic instrument that is faster than prior art systems and methods to provide updated output at a higher frequency.

It is another object of the present invention to provide a position detection system for an ophthalmic instrument that is relatively inexpensive to manufacture.

It is yet another object of the present invention to provide a position detection system for an ophthalmic instrument and a method for calibrating the system, whereby the system can be calibrated easily and periodically after manufacture to ensure accuracy.

It is yet another object of the present invention to provide a position detection system for an ophthalmic instrument that cooperates with an instructive display for presenting alignment cues to an operator.

In furtherance of these and other objects, an ophthalmic instrument incorporates an afocal position detection system for determining X-Y-Z alignment status of the instrument relative to a patient's eye. In a preferred embodiment, the position detection system comprises first and second light sources on opposite sides of a central optical axis of the instrument, and corresponding first and second light-sensitive area detectors positioned to receive light from an associated light source after it has been reflected by the cornea. The detectors provide signal information indicative of the local x-y position of an illumination spot formed thereon. In a preferred embodiment, the first and second detectors are quad-cell detectors having four quadrants, and the illumination spot size is about the size of one quadrant, whereby the x-y position can be determined based on the four signal levels generated by the quadrants. Collector lenses after each light source and in front of each detector minimize vergence in the light beam as it illuminates the eye and as it arrives at a detector.

The local x-y data from each detector are then provided as input to a series of stored geometrical relationships determined during instrument calibration for giving the X-Y-Z global alignment status of the instrument relative to the eye. The geometrical relationships are multiple regression equations for X, Y, and Z, wherein regression coefficients for each equation are determined by reading local x-y data from the detectors for an artificial eye placed at a plurality of known X-Y-Z positions during calibration. The regression coefficients are stored during calibration and used during normal instrument operation to quickly calculate X, Y and Z coordinates based on local x-y data from the detectors as an operator positions the instrument relative to a patient's eye.

A "heads-up" display is preferably connected to receive the X-Y-Z position data and provide instructional cues to the operator for moving the instrument to achieve alignment. In a current embodiment, the heads-up display comprises a polar array of light emitting diodes selectively illuminated to indicate a desired X-Y movement direction, and a linear array of light emitting diodes selectively illuminated to indicate a desired Z movement direction. An image of the heads-up display is presented to the operator along the instrument optical axis through the use of a beamsplitter that allows a macro-image of the patient's eye to be transmitted as well along the optical axis, whereby the X-Y polar array is arranged circumferentially about the macro-image.

BRIEF DESCRIPTION OF THE SEVERAL VIEWS OF THE DRAWINGS

The nature and mode of operation of the present invention will now be more fully described in the following detailed description of the invention taken with the accompanying drawing figures, in which.

DESCRIPTION OF THE INVENTION

Figure 1:
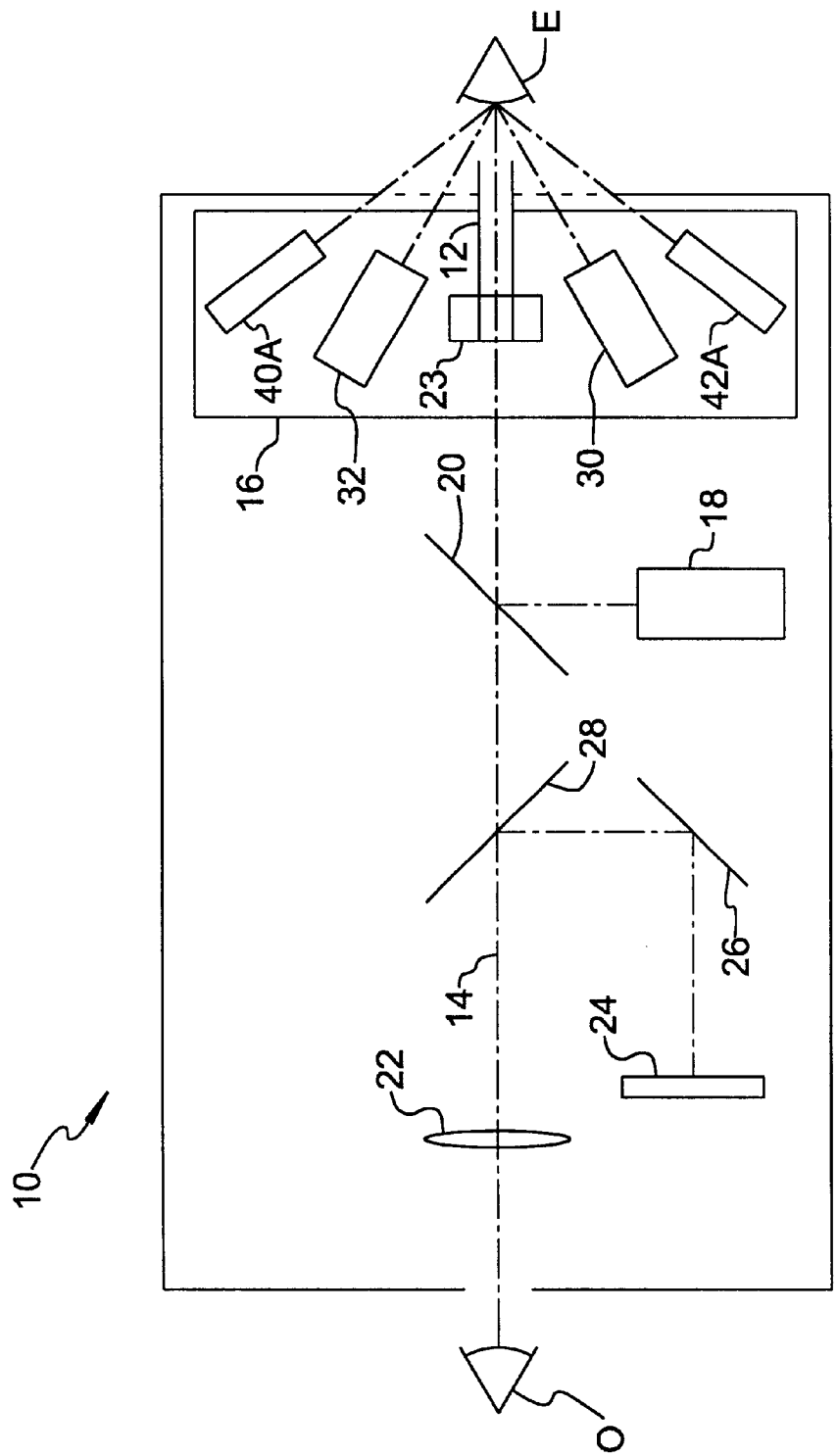
FIG. 1 is an optical schematic diagram of an ophthalmic instrument incorporating a position detection system of the present invention.

FIG. 1, an ophthalmic instrument incorporating a position detection system of the present invention is illustrated schematically and identified by the reference numeral 10. Instrument 10 is depicted as being a non-contact tonometer operable to discharge a fluid pulse through a fluid discharge tube 12 to cause observable deformation of a patent's cornea for purposes of measuring intraocular pressure. However, the present invention may be implemented in other types of ophthalmic instruments where it is necessary to ascertain the X-Y-Z alignment status of the instrument relative to an eye.

Instrument 10 includes an optical axis 14 along which discharge tube 12 is aligned, a nosepiece 16 fixed near a front portion of the instrument for mounting various optical and opto-electronic elements of the instrument as described below, a fixation target projecting system 18 cooperating with a beamsplitter 20 to present a visible fixation target to the patient along optical axis 14, an eyepiece 22 and a macro-lens 23 for enabling an operator O to view the patient's eye E through the instrument along optical axis 14, a heads-up display 24, and a mirror 26 cooperating with a beamsplitter 28 to present an image of the heads-up display to the operator along optical axis 14. Macro-lens 23 is preferably a planar—planar lens such that the operator sees the eye in an unmagnified state, however it is possible to use a macro-lens having optical power to provide some other desired field of view with respect to the eye.

Attention is directed now to the elements mounted in nosepiece 16. As mentioned above, instrument 10 is illustrated as being a non-contact tonometer, and thus it includes an applanation emitter 30 for obliquely illuminating the eye during discharge of the fluid pulse, and an applanation detector 32 arranged on an opposite side of the eye for receiving light reflected from the cornea and registering a peak signal at the moment the corneal surface is flattened ("applanated") by the fluid pulse. Those familiar with the non-contact tonometers will recognize that applanation emitter 30 and applanation detector 32 are parts of a well-known prior art arrangement for determining the moment applanation occurs based on reflected light from the corneal surface.

Also within nosepiece 16 are elements of a position detection system according to an embodiment of the present invention. More specifically, the schematic representation of FIG. 1 shows light source 40A on one side of optical axis 14 and a detector 42A on an opposite side of optical axis 14 used for position detection. In actual practice, nosepiece 16 supports a second light source 40B and a second detector 42B, which can be seen in the view of FIG. 2. In the embodiment described at present, light sources 40A and 40B are located just below the horizontal plane containing optical axis 14, while detectors 42A and 42B are located just above the horizontal plane containing optical axis 14, thereby leaving space in the horizontal plane for applanation emitter 30 and applanation detector 32. First light source 40A directs a first beam of light along a first illumination axis 41A for illuminating eye E, and first detector 42A defines a first light-detecting area for receiving an image of first light source 40A formed by light reflected from the eye. Light traveling along first illumination axis 41A passes through a collector lens 44A and is obliquely incident to the generally spherical surface of the cornea, where it is reflected toward first detector 42A. A collector lens 46A in front of first detector 42A substantially collimates the divergent beam coming from the generally spherical surface of the cornea, whereby a spot of illumination is received on the light-detecting area defined by first detector 42A. Essentially, first detector 42A detects an apparent or virtual source behind the cornea. Second light source 40B, second illumination axis 41B, collector lenses 44B and 46B, and second detector 42B form a similar system, and are preferably arranged in opposing symmetry about the vertical plane containing optical axis 14. In a preferred construction, position light sources 40A and 40B and applanation emitter 30 are infrared light-emitting diodes for invisibility to the patient, and are mounted or formed on a single flexible circuit board to allow assembly of the instrument with greater ease. Similarly, first and second detectors 42A, 42B are preferably carried by a flexible circuit board for easy assembly.

Figure 2:
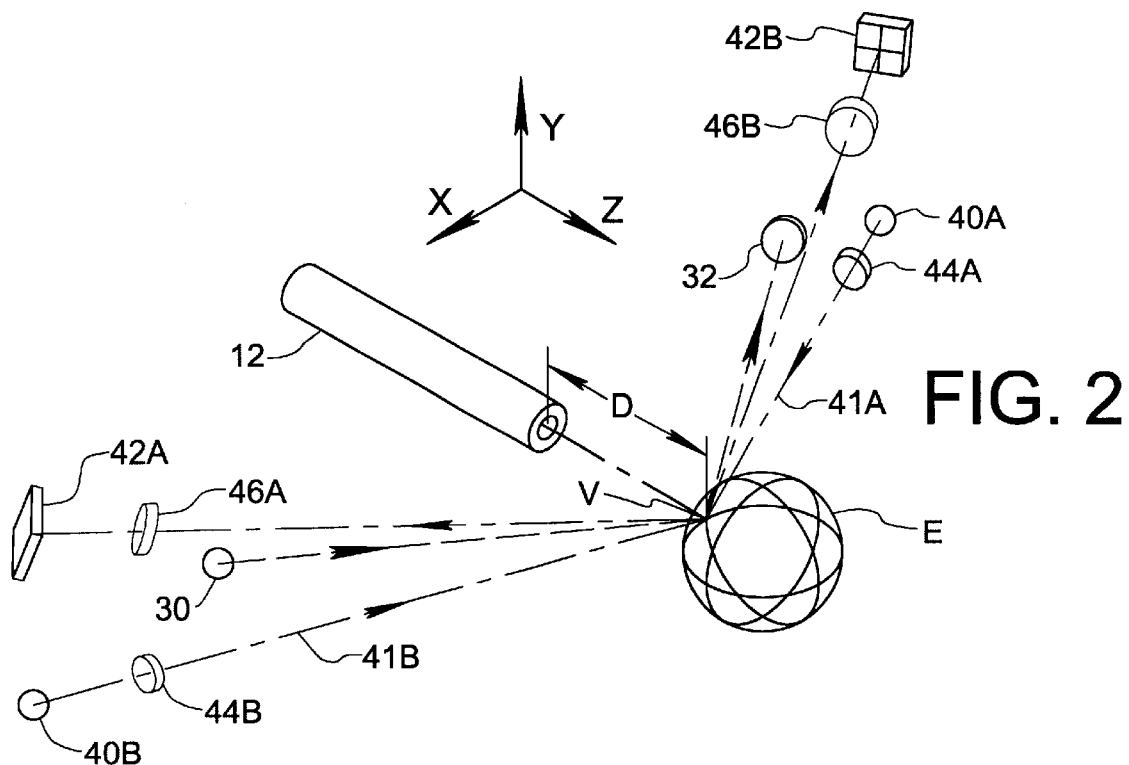
FIG. 2 is a schematic perspective view showing the arrangement of elements of a position detection system formed in accordance with a preferred embodiment of the present invention.

In the illustration of FIG. 2, the instrument as represented by the exit end of fluid discharge tube 12 and the eye as represented by the corneal vertex V are shown in a state of three-dimensional (X-Y-Z) alignment. In the present embodiment, alignment is achieved when optical axis 14 intersects and is normal to corneal vertex V, and the exit end of fluid discharge tube 12 is a predetermined firing distance D away from corneal vertex V in a Z-axis direction. The orientation of first detector 42A and that of second detector 42B are chosen such that the central ray of the corresponding corneally reflected illumination beam is normal to the light-detecting area of the associated detector and arrives substantially at a central point of the light-detecting area when X-Y-Z alignment exists.

Figure 3:
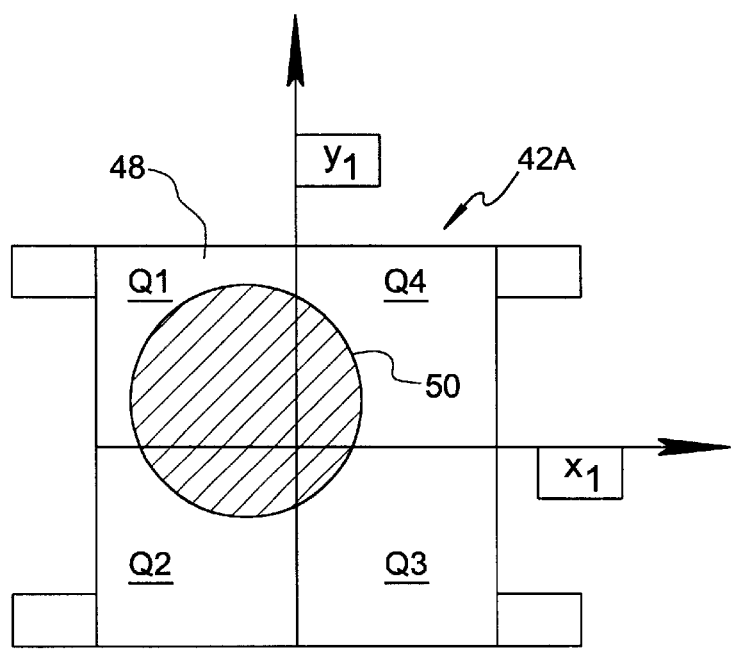
FIG. 3 is a detail view of a quad-cell detector used in practicing the preferred embodiment of the present invention, annotated to illustrate mathematical nomenclature referenced in the present specification.

FIG. 3 shows a light-detecting area 48 of first detector 42A, with the understanding that the accompanying description also applies as well to second detector 42B. An image of light source 40A appears as a spot 50 on light detecting area 48. In the present embodiment, first detector 42A is a quad-cell detector comprising four quadrants Q1, Q2, Q3, and Q4 each providing a signal proportional to the illumination optical power received thereby. The size of each quadrant is preferably on the order of about 1.3 mm×1.3 mm, with a separation distance of about 0.1 mm between adjacent quadrant edges. The size of illumination spot 50 should be on the order of the size of one quadrant for meaningful x-y resolution. The size of illumination spot 50 will change during Z-axis adjustment as instrument 10 is moved closer to or further away from the eye. Moreover, the rate of change in spot size increases as the instrument moves closer to the eye. Therefore, it is desirable to optimize the system for a range of Z-axis positions centered about the predetermined firing distance D (i.e.+/−2.00 mm) such that the change in spot size for Z-axis positions throughout the range is minimized. Optimization can be carried out by selecting an appropriate front focal length for collector lenses 46A, 46B that causes the light striking detectors 42A, 42B to transition from being slightly convergent to being slightly divergent as the instrument is moved through the range of Z-axis positions toward the eye, wherein the light striking detectors 42A, 42B is approximately collimated when the instrument is at the predetermined firing distance D. In practice, it has been found that the firing distance D should be just beyond the front focal length of collector lenses 46A, 46B.

As will be understood, the signals from quadrants Q1–Q4 of first detector 42A are indicative of the local two-dimensional location ($x_1$, $y_1$) of the centroid of spot image 50 in light detecting area 48, and the signals from quadrants Q1–Q4 of second detector 42B are indicative of the local two-dimensional location ($x_2$, $y_2$) of a similar spot formed on the light detecting area of the second detector. The local x position is given by comparing the signal strengths from each quadrant as follows:

$$x=(Q3+Q4-Q1-Q2)/(Q1+Q2+Q3+Q4).$$

Likewise, the local y position is given by comparing the signal strengths from each quadrant as follows:

$$y=(Q1+Q4-Q2-Q3)/(Q1+Q2+Q3+Q4).$$

Figure 4:
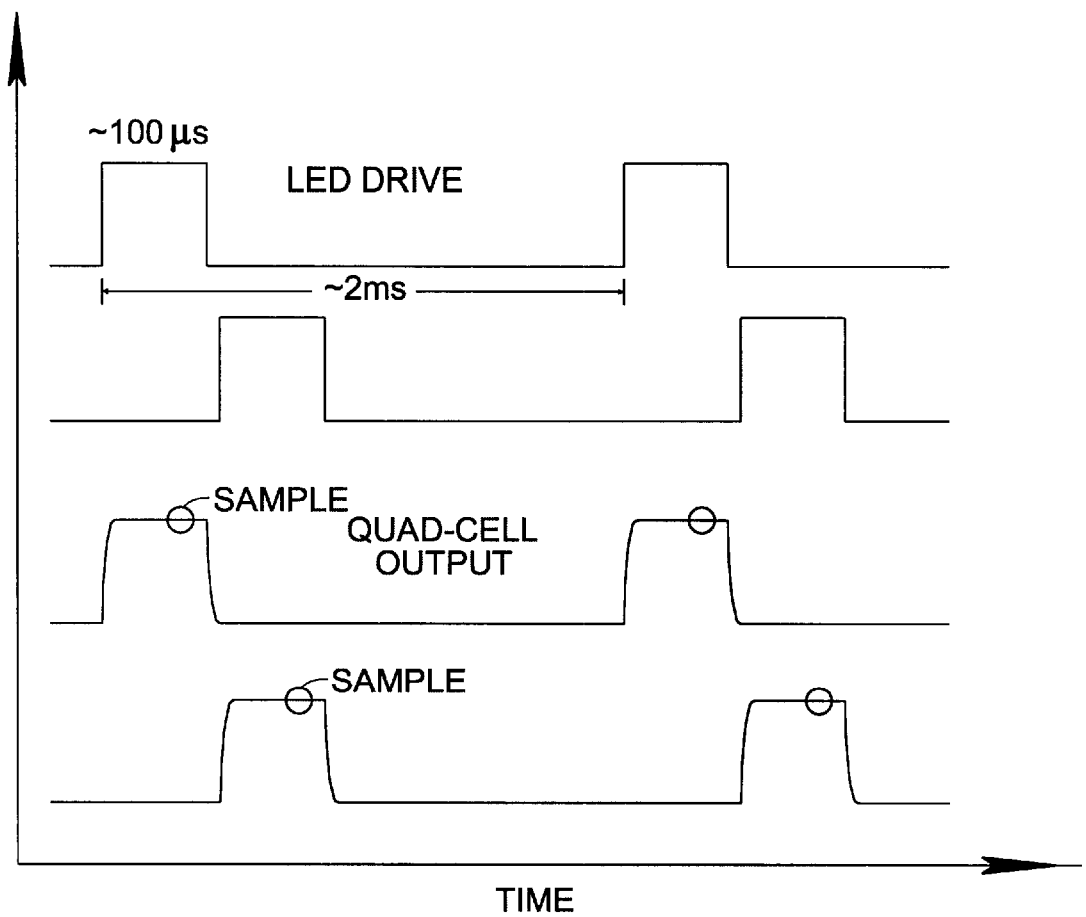
FIG. 4 is an electronic timing diagram relating to illumination and sampling of the quad-cell detector shown in FIG. 3.

In order to avoid interference, provide sufficient illumination intensity, and reduce power consumption, first light source 40A and second light source 40B are illuminated sequentially, and first detector 42A and second detector 42B are sampled sequentially. FIG. 4 is a timing diagram which illustrates that one light source is pulsed for a duration of about 100 μs and then sampled, and then the other light source is pulsed for the same duration and sampled. The cycle is repeated at approximately every 2 ms.

Figure 5:
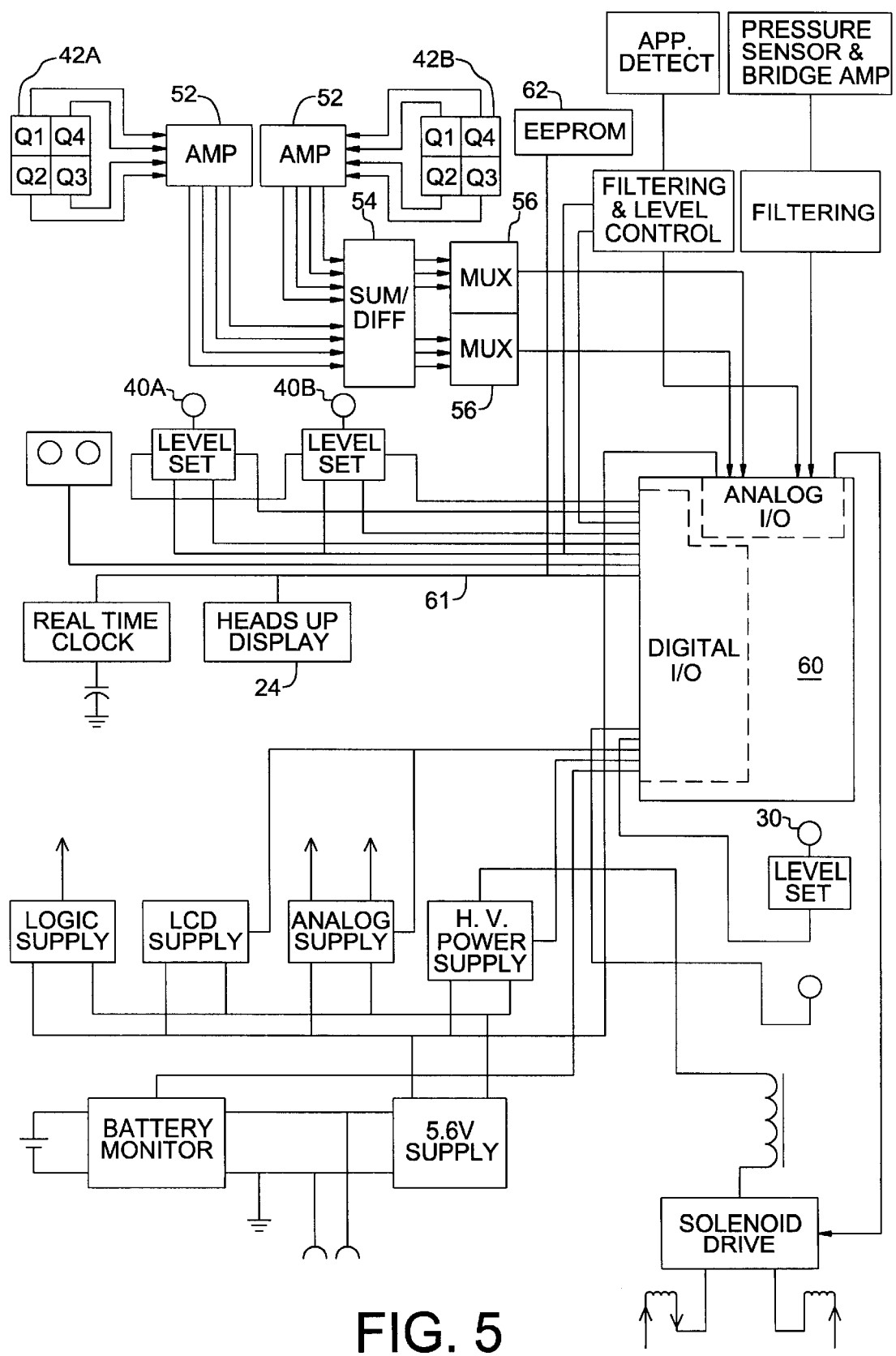
FIG. 5 is an electronic block diagram of the ophthalmic instrument shown in FIG. 1.

Referring also now to FIG. 5, the analog signals from quadrants Q1–Q4 of detectors 42A, 42B are fed to amplifiers 52 and then input to a sum/difference circuit 54. Sum/difference circuit 54 provides three outputs for each position detector 42A, 42B. Two of the outputs are the respective x and y numerators in the above equations, and the third output is the denominator common to both equations. The output signals are multiplexed by a multiplexor 56 and then provided as analog input to a microprocessor 60, which provides on-board analog-to-digital conversion of the signals. Microprocessor 60 is programmed to calculate the final spot locations ($x_1$, $y_1$) and ($x_2$, $y_2$).

While the present embodiment is described as employing quad-cell detectors, it is possible to substitute other detector types and configurations for purposes of the present invention. For example, a variety of position sensitive devices (PSDs) are commercially available that can provide local x-y signal information. Also, it is possible to arrange four discrete photosensitive detectors in a quadrant configuration to mimic the quad-cell detector described above.

The global X-Y-Z alignment status of ophthalmic instrument 10 relative to the eye is then computed by inputting coordinates $x_1$, $y_1$ from first detector 42A and coordinates $x_2$, $y_2$ from second detector 42B to a plurality of predetermined geometric relationships stored in memory 62 during calibration of instrument 10. More specifically, geometrical relationships giving the global position coordinates X, Y, and Z can be determined by multiple regression as follows:

$$X=R_1x_1+R_2y_1+R_3x_2+R_4y_2+R_5,$$

$$Y=R_6x_1+R_7y_1+R_8x_2+R_9y_2+R_{10},$$

and $$Z=R_{11}x_1+R_{12}y_1+R_{13}x_2+R_{14}y_2+R_{15},$$

wherein the regression coefficients $R_1$–$R_{15}$ are found during instrument calibration measurements using an artificial eye.

Figure 6:
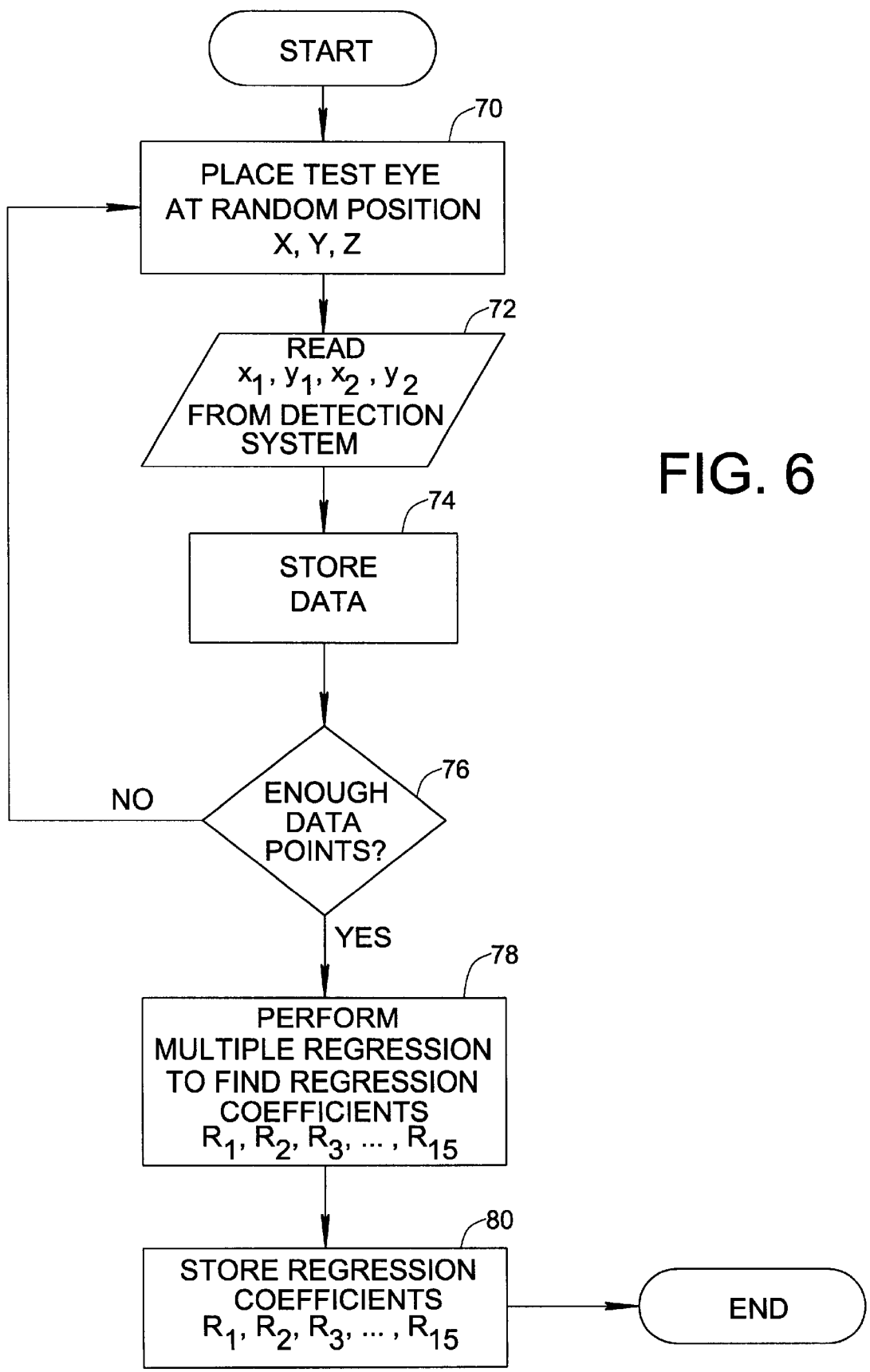
FIG. 6 is a flow diagram of steps followed to calibrate the position detection system of the present invention.

FIG. 6 is a flow diagram showing the steps followed to calibrate the position detection system of the present invention. First, according to step 70, an artificial "test" eye is placed at a random, known position X, Y, Z relative to instrument 10. Then, as indicated by steps 72 and 74, the local spot positions ($x_1$, $y_1$) and ($x_2$, $y_2$) are read from the position detection system and stored in a table with the corresponding known global coordinates X, Y, Z. If a sufficient number of data points have been measured according to query 76, multiple regression is performed in step 78 to find the regression coefficients $R_1$–$R_{15}$, which are then stored in memory pursuant to step 80. If more data points are needed according to query 76, the process returns to step 70 and is repeated. It is preferable to calibrate the position detection system using a large number random locations of the artificial eye, as this will provide greater accuracy in the determination of the regression coefficients, and ultimately provide improved accuracy in the computed X, Y, Z location of a patient's eye.

Primarily because the position detection system of the present invention obviates the need for scanning a CCD array having a large number of pixels, it provides X-Y-Z alignment status information at a much higher repetition rate than systems of the prior art. As noted above, a faster system is particularly useful for alignment of hand-held instruments, which may be actuated to take a measurement as soon as X-Y-Z alignment is confirmed. Thus, the system reduces the lag time between confirmation of alignment and measurement during which further relative movement between the instrument and eye can occur. Moreover, the position detection system of the present invention can be calibrated periodically by manufacturer personnel to ensure alignment accuracy.

Figure 7:
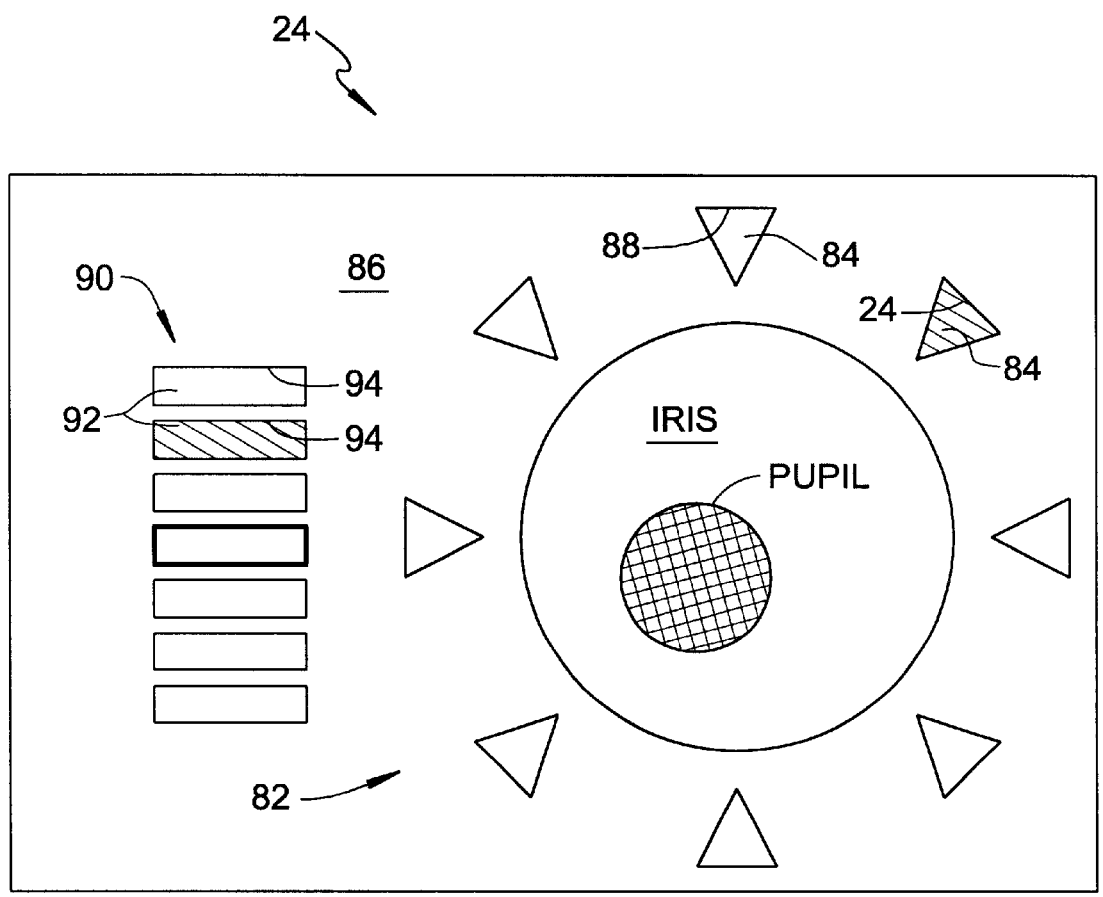
FIG. 7 is an enlarged view of a heads-up display of the ophthalmic instrument shown in FIG. 1 for providing alignment instructions to an operator for aligning the instrument relative to an eye to be tested.

FIG. 7 shows an enlarged view of "heads-up" display 24 of instrument 10 as it appears to an operator viewing through eyepiece 22 along optical axis 14. Display 24 assists the operator in aligning the instrument by presenting the computed X-Y-Z alignment status in a format that instructs the operator regarding movement of the instrument necessary to achieve alignment. Heads-up display 24 comprises a polar array 82 of light-emitting diodes 84 masked by an overlay 86 having light-transmitting directional pointers 88 for providing an X-Y alignment instruction to the operator. The LEDs 84 in polar array 82 are each connected to microprocessor 60 by way of an I²C line 61 and a serial-to-parallel converter (not shown), whereby the LEDs are selectively illuminated depending upon the X-Y alignment status of the instrument relative to the eye. In particular, an LED 84 is illuminated corresponding to an appropriate directional pointer instructing the operator of the direction to move the instrument to align optical axis 14 with corneal vertex V. When X-Y alignment is achieved, all the LEDs 84 in polar array 82 can be illuminated in continuous or pulsing fashion to communicate a condition of X-Y alignment to the operator. Heads-up display 24 further comprises a linear array 90 of light-emitting diodes 92 positioned to correspond with light-transmitting rectangles 94 in overlay 86 for purposes of Z-axis alignment. The LEDs 92 in linear array 90 are each connected to microprocessor 60 by way of I²C line 61 and a serial-to-parallel converter (not shown), whereby the LEDs are selectively illuminated depending upon the Z alignment status of the instrument relative to the eye. More specifically, and by way of non-limiting example, the top and bottom LEDs in linear array 90 are the same color (i.e. red), the middle LED is another color (i.e. green), and the LEDs between the top Led and middle LED and between the bottom LED and the middle LED are all yet another color (i.e. yellow). When the instrument is too close to the eye, both red LEDs flash as a warning to the operator. The lower red and yellow LEDs indicate the instrument should be moved away from the eye, while the upper red and yellow LEDs indicate the instrument should be moved toward the eye. The green LED indicates that Z-axis alignment is reached. Currently, it is preferred to provide LEDs 84 and 92 on a single circuit board, and to use photographic film to form overlay 86, which may be separated from the LED circuit board by a spacer (not shown).

As can be seen in FIG. 1, the actual heads-up display 24 is located in the instrument at a location off of optical axis 14. An image of heads-up display 24 is presented to the operator along optical axis 14 by means of mirror 26 and beamsplitter 28. The X-Y polar array 82 is arranged circumferentially about a macro image of the patient's eye through macro-lens 23, whereby the operator can see the pupil and surrounding iris along with superimposed instructional display cues provided by heads-up display 24. For example, in FIG. 7, the operator is being instructed to move the instrument lower and to the left for X-Y alignment, and closer to the eye for Z alignment.

What is claimed is:

1. A position detection system for determining the X-Y-Z alignment status of an ophthalmic instrument relative to an eye of a patient, said position detection system comprising:
   a first light source for illuminating said eye with a first beam of light along a first illumination axis;
   a second light source for illuminating said eye with a second beam of light along a second illumination axis different from said first illumination axis;
   a first detector defining a first light-detecting area for receiving an image of said first light source, said first detector providing signal information indicative of the location of said image of said first light source in said first light detecting area;
   a second detector defining a second light-detecting area for receiving an image of said second light source, said second detector providing signal information indicative of the location of said image of said second light source in said second light detecting area;
   processing means connected to said first and second detectors for receiving said signal information from said first and second detectors, determining first coordinates $x_1$, $y_1$ describing the location of said image of said first light source in said first light detecting area and second coordinates $x_2$, $y_2$ describing the location of said image of said second light source in said second light detecting area, and computing the X, Y, and Z alignment status of said ophthalmic instrument relative to said eye by inputting said first coordinates $x_1$, $y_1$ and said second coordinates $x_2$, $y_2$ to a plurality of predetermined geometric relationships; and
   memory means connected to said processing means for storing said plurality of predetermined geometric relationships.

2. The position detection system according to claim 1, wherein said system is an afocal system wherein said first beam of light lacks a focal point between said first light source and said eye and between said eye and said first detector and said second beam of light lacks a focal point between said second light source and said eye and between said eye and said second detector.

3. The position detection system according to claim 1, wherein said first detector comprises a quad-cell detector having four quadrants each providing a signal proportional to the illumination optical power received thereby.

4. The position detection system according to claim 3, wherein said second detector comprises a quad-cell detector having four quadrants each providing a signal proportional to the illumination optical power received thereby.

5. The position detection system according to claim 4, wherein said four quadrants of said second detector are the same size, and said image of said second light source in said second light detecting area is a substantially circular image having an area approximately equal to the area of one of said four quadrants of said second detector.

6. The position detection system according to claim 3, wherein said four quadrants of said first detector are the same size, and said image of said first light source in said first light detecting area is a substantially circular image having an area approximately equal to the area of one of said four quadrants of said first detector.

7. The position detection system according to claim 1, wherein said first detector comprises a plurality of individual photosensitive detectors arranged to collectively define said first light-detecting area, each of said plurality of individual photosensitive detectors providing a signal proportional to the illumination optical power received thereby.

8. The position detection system according to claim 7, wherein said second detector comprises a plurality of individual photosensitive detectors arranged to collectively define said second light-detecting area, each of said plurality of individual photosensitive detectors providing a signal proportional to the illumination energy received thereby.

9. The position detection system according to claim 1, wherein said first detector comprises a position sensitive detector.

10. The position detection system according to claim 9, wherein said second detector comprises a position sensitive detector.

11. The position detection system according to claim 1, wherein said ophthalmic instrument comprises an optical axis, and said first and second illumination axes are symmetrical arranged about said optical axis.

12. The position detection system according to claim 1, wherein said ophthalmic instrument comprises a optical axis, and said first and second illumination axes are symmetrically arranged about said optical axis.

13. The position detection system according to claim 1, wherein a central ray of said first beam of light is obliquely incident to a corneal vertex of said eye when said ophthalmic instrument is in X-Y-Z alignment relative to said eye.

14. The position detection system according to claim 13, wherein said first detector is arranged such that said central ray of said first beam of light is normal to said first light-detecting area after reflection of said first beam of light by said eye when said ophthalmic instrument is in X-Y-Z alignment relative to said eye.

15. The position detection system according to claim 14, wherein a central ray of said second beam of light is obliquely incident to said corneal vertex of said eye when said ophthalmic instrument is in X-Y-Z alignment relative to said eye.

16. The position detection system according to claim 15, wherein said second detector is arranged such that said central ray of said second beam of light is normal to said second light-detecting area after reflection of said second beam of light by said eye when said ophthalmic instrument is in X-Y-Z alignment relative to said eye.

17. The position detection system according to claim 1, further comprising a display connected to said processing means for reporting said computed X-Y-Z alignment status to an operator.

18. The position detection system according to claim 17, wherein said display is an instructive display for guiding said operator in achieving X-Y-Z alignment of said ophthalmic instrument relative to said eye.

19. The position detection system according to claim 18, wherein said instructive display includes a polar array of light-emitting diodes for providing an X-Y alignment instruction to said operator.

20. The position detection system according to claim 18, wherein said instructive display includes a linear array of light-emitting diodes for providing a Z alignment instruction to said operator.

21. A method for determining the X-Y-Z alignment status of an ophthalmic instrument relative to an eye of a patient, said method comprising the steps of:
A) illuminating said eye with light from first and second light sources;
B) detecting an image of said first light source on a first light-detecting area and detecting an image of said second light source on a second light-detecting area;
C) determining first coordinates $x_1$, $y_1$ describing the location of said image of said first light source in said first light detecting area and second coordinates $x_2$, $y_2$ describing the location of said image of said second light source in said second light detecting area; and
D) calculating X, Y, and Z coordinates of said eye by inputting said first coordinates $x_1$, $y_1$ and said second coordinates $x_2$, $y_2$ to a plurality of predetermined geometric relationships.

22. The method according to claim 21, wherein said first and second light sources are illuminated sequentially in said step (A), and said images of said first and second light sources are detected sequentially in said step (B).

23. The method according to claim 21, wherein said step (B) is performed using first and second quad-cell detectors for detecting said image of said first light source and said image of said second light source, respectively.

24. A method for calibrating a position detection system for determining the X, Y, and Z alignment status of an ophthalmic instrument relative to an eye of a patient, said method comprising the steps of:
A) positioning a reference eye at a known random position X, Y, Z relative to said ophthalmic instrument;
B) illuminating said eye with light from first and second light sources;
B) detecting an image of said first light source on a first light-detecting area and detecting an image of said second light source on a second light-detecting area;
C) determining first coordinates $x_1$, $y_1$ describing the location of said image of said first light source in said first light detecting area and second coordinates $x_2$, $y_2$ describing the location of said image of said second light source in said second light detecting area;
D) recording said known position X, Y, Z said first coordinates $x_1$, $y_1$, and said second coordinates $x_2$, $y_2$;
E) repeating said steps (A) through (D) for a plurality of times; and
F) formulating geometric relationships giving X, Y, and Z positions of said ophthalmic instrument relative to said eye as a function of first coordinates $x_1$, $y_1$ and second coordinates $x_2$, $y_2$; and
G) storing said geometric relationships.

* * * * *